United States Patent
Nagano et al.

(10) Patent No.: US 8,143,069 B2
(45) Date of Patent: Mar. 27, 2012

(54) FLUORESCENT PROBE AND METHOD OF MEASURING HYPOCHLORITE ION

(75) Inventors: Tetsuo Nagano, Tokyo (JP); Yasuteru Urano, Kanagawa (JP); Suguru Kenmoku, Tokyo (JP)

(73) Assignee: The University of Tokyo, Tokyo (JP)

( * ) Notice: Subject to any disclaimer, the term of this patent is extended or adjusted under 35 U.S.C. 154(b) by 72 days.

(21) Appl. No.: 12/279,881

(22) PCT Filed: Mar. 1, 2007

(86) PCT No.: PCT/JP2007/053960
§ 371 (c)(1),
(2), (4) Date: Jun. 25, 2009

(87) PCT Pub. No.: WO2007/100061
PCT Pub. Date: Sep. 7, 2007

(65) Prior Publication Data
US 2009/0317914 A1    Dec. 24, 2009

(30) Foreign Application Priority Data
Mar. 3, 2006  (JP) .................... 2006-057792

(51) Int. Cl.
*G01N 33/00*   (2006.01)
*G01N 21/64*   (2006.01)
*C07D 311/82*  (2006.01)
*C07D 409/04*  (2006.01)

(52) U.S. Cl. ........ 436/124; 436/101; 436/125; 436/166; 436/172; 503/221; 549/9; 549/13; 549/49; 549/58; 549/60; 549/74; 549/223; 549/227; 549/331; 549/381; 549/385; 549/388; 549/394

(58) Field of Classification Search .................. 436/101, 436/124–125, 127, 166, 172; 549/223, 227, 549/9, 13, 49, 58, 60, 74–75, 78, 80, 331, 549/381, 385, 388, 394; 568/38–39, 44; 503/221

See application file for complete search history.

(56) References Cited

U.S. PATENT DOCUMENTS

| | | | | |
|---|---|---|---|---|
| 3,244,548 A * | 4/1966 | Sullivan | ........................ | 503/203 |
| 3,244,549 A * | 4/1966 | Farnham et al. | ............. | 503/201 |
| 3,244,728 A | 4/1966 | Johnson et al. | | |
| 3,733,337 A * | 5/1973 | Heinz et al. | ..................... | 549/26 |
| 3,792,481 A * | 2/1974 | Nagashima et al. | .......... | 503/204 |
| 3,876,659 A * | 4/1975 | Houlihan et al. | ............. | 548/409 |
| 3,880,656 A * | 4/1975 | Nagashima et al. | ........ | 430/120.4 |
| 4,390,616 A * | 6/1983 | Sato et al. | ..................... | 430/338 |
| 4,407,960 A * | 10/1983 | Tratnyek | .......................... | 436/1 |
| 4,433,156 A * | 2/1984 | Ishige et al. | ................... | 549/227 |
| 4,727,056 A * | 2/1988 | Sano et al. | ..................... | 503/218 |
| 4,970,309 A | 11/1990 | King | | |
| 5,028,725 A | 7/1991 | King | | |
| 5,196,297 A | 3/1993 | Dombrowski, Jr. et al. | | |
| 5,220,036 A | 6/1993 | King | | |
| 5,874,590 A * | 2/1999 | Nagano et al. | ................ | 549/223 |
| 2001/0001800 A1* | 5/2001 | Nagano et al. | ................ | 549/227 |
| 2004/0043498 A1 | 3/2004 | Nagano et al. | | |
| 2005/0123478 A1 | 6/2005 | Nagano et al. | | |
| 2008/0014147 A1 | 1/2008 | Nagano et al. | | |

FOREIGN PATENT DOCUMENTS

| | | |
|---|---|---|
| JP | 63-501941 | 8/1988 |
| WO | 87/03541 | 6/1987 |
| WO | 01/64664 | 9/2001 |
| WO | 02/18362 | 3/2002 |

OTHER PUBLICATIONS

K. Setsukinai et al., "Development of Novel Fluorescence Probes That Can Reliably Detect Reactive Oxygen Species and Distinguish Specific Species," The Journal of Biological Chemistry, vol. 278, No. 5, 2003, pp. 3170-3175.

M. Suematsu et al., "In Vivo Visualization of Oxyradical-Dependent Photoemission during Endotheluim-Granulocyte Interaction in Microvascular Beds Treated with Platelet-Activating Factor," The Journal of Biochemistry, vol. 106, 1989, pp. 355-360.

* cited by examiner

*Primary Examiner* — Arlen Soderquist

(74) *Attorney, Agent, or Firm* — Greenblum & Bernstein, PLC

△ No treatment
☐ Hydrogen peroxide 1 mmol/L
◇ Hydrogen peroxide 100 mmol/L
○ Sodium hypochlorite 2.5 μmol/L

(57) ABSTRACT

A compound represented by the following general formula (II):

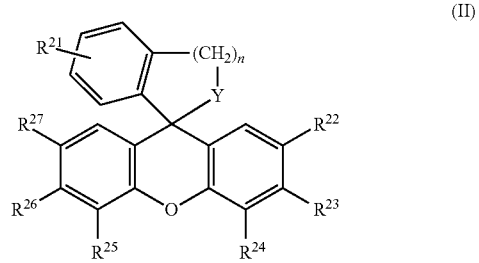

(II)

wherein $R^{21}$ represents hydrogen atom or one to four monovalent substituents substituting on the benzene ring, and when $R^{21}$ represents two or more substituents, the substituents may be the same or different; $R^{22}$, $R^{24}$, $R^{25}$, and $R^{27}$ independently represent hydrogen atom, or a monovalent substituent; $R^{23}$ represents —OH or —N($R^{28}$)($R^{29}$) (wherein $R^{28}$ and $R^{29}$ independently represent an alkyl group which may be substituted); $R^{26}$ represents —N($R^{30}$)($R^{31}$) (wherein $R^{30}$ and $R^{31}$ independently represent an alkyl group which may be substituted); n represents an integer of 1 to 3; and Y represents —S— or —O—, which is useful for selective measurement of hypochlorite ion.

3 Claims, 6 Drawing Sheets

[Fig. 1]
(A)
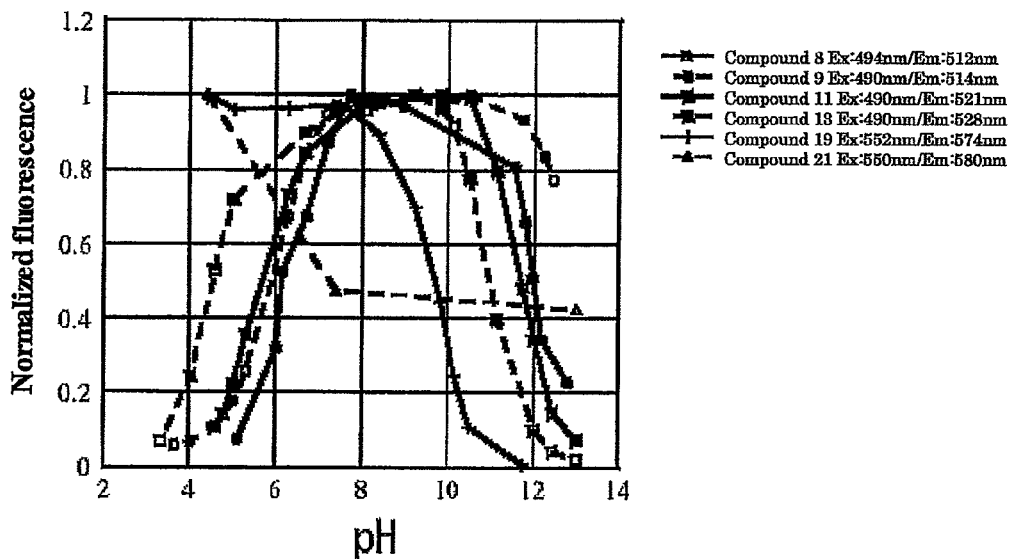
(B)
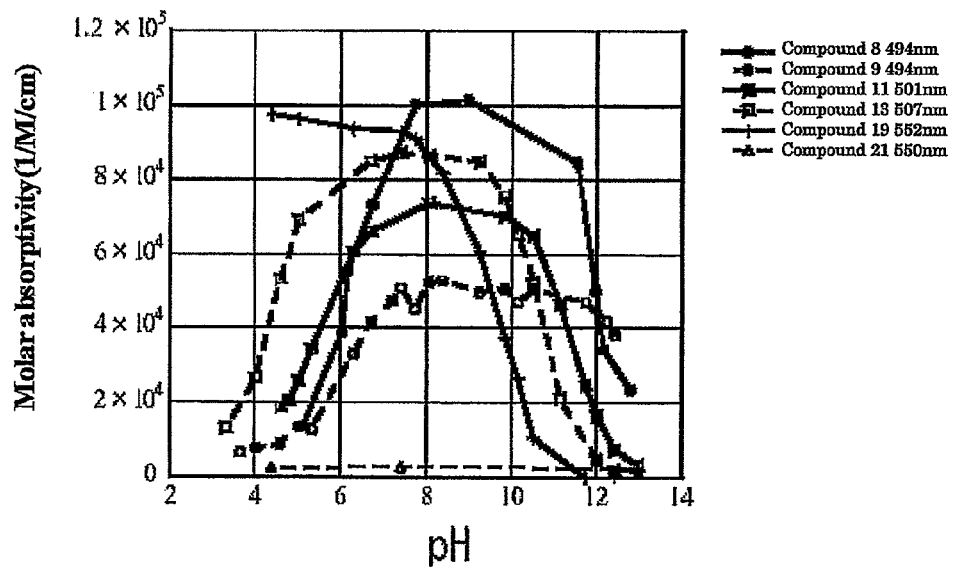

[Fig. 2]
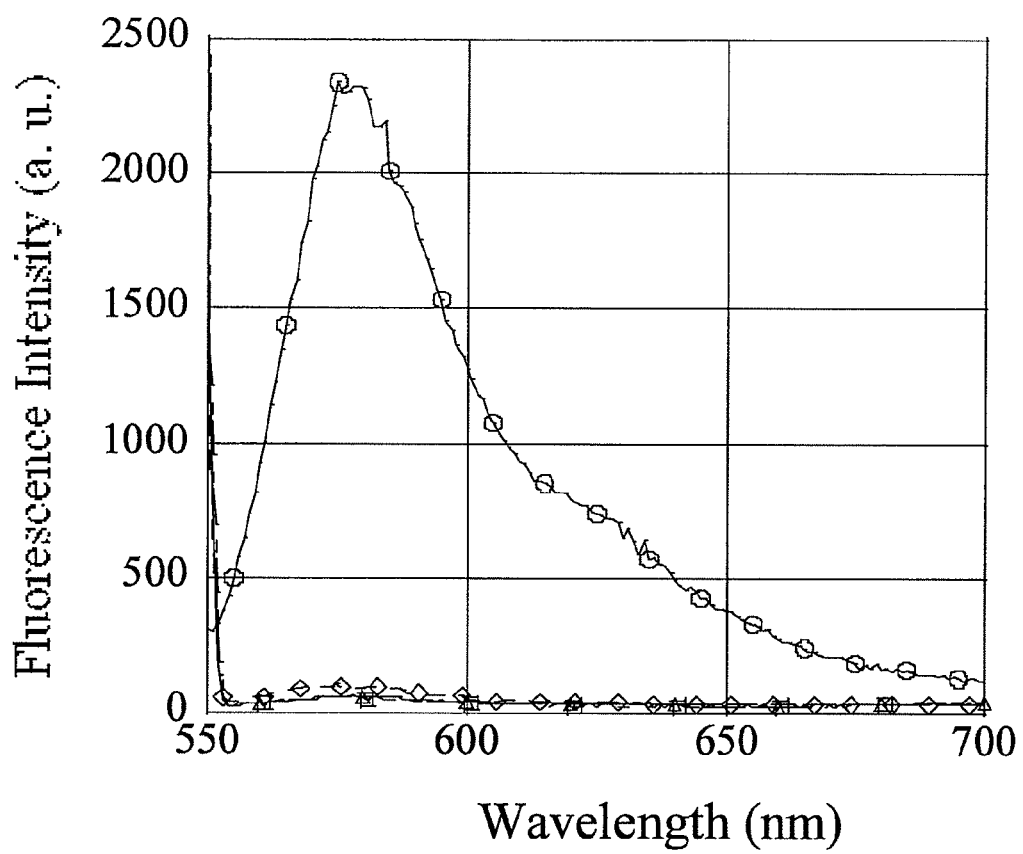
△ No treatment
☐ Hydrogen peroxide 1 mmol/L
◇ Hydrogen peroxide 100 mmol/L
○ Sodium hypochlorite 2.5 μmol/L

[Fig. 3]
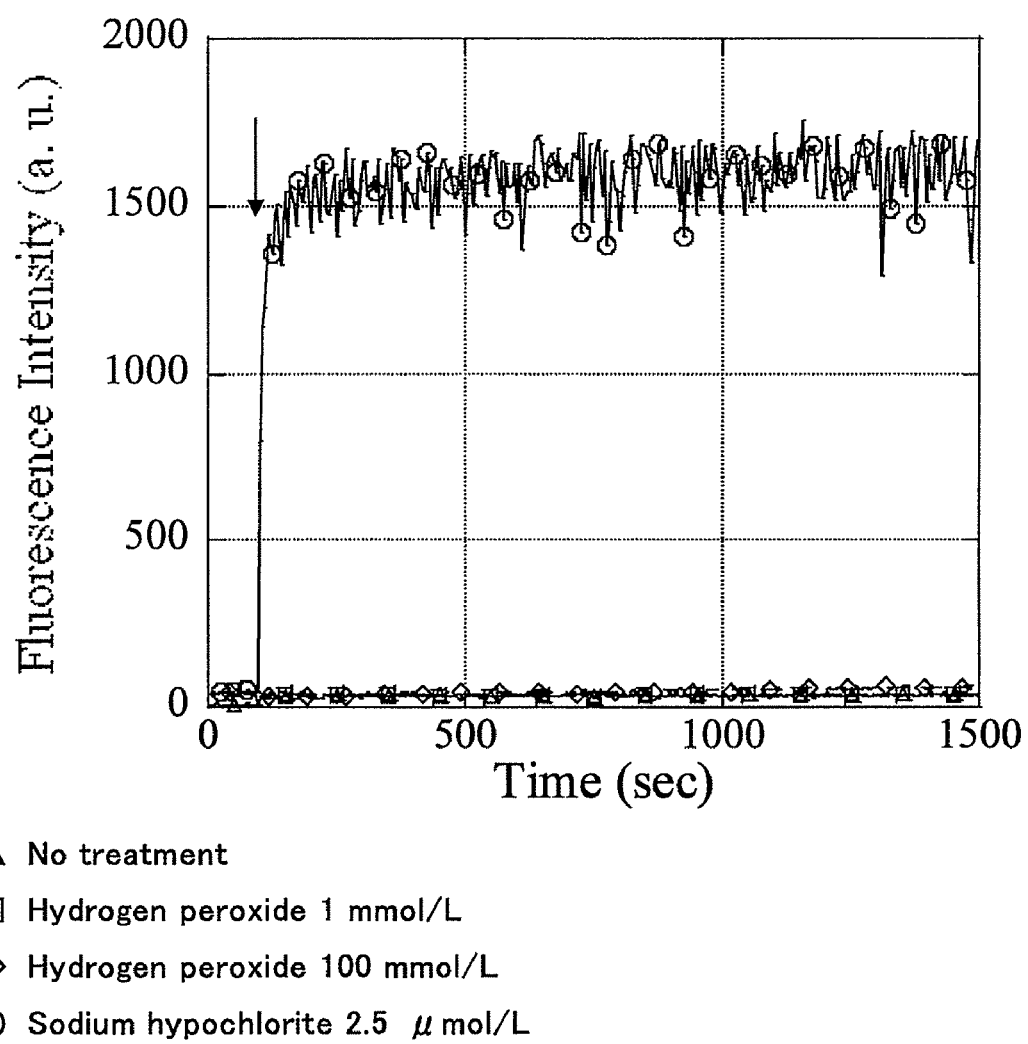
△ No treatment
□ Hydrogen peroxide 1 mmol/L
◇ Hydrogen peroxide 100 mmol/L
○ Sodium hypochlorite 2.5 $\mu$mol/L

[Fig. 4]
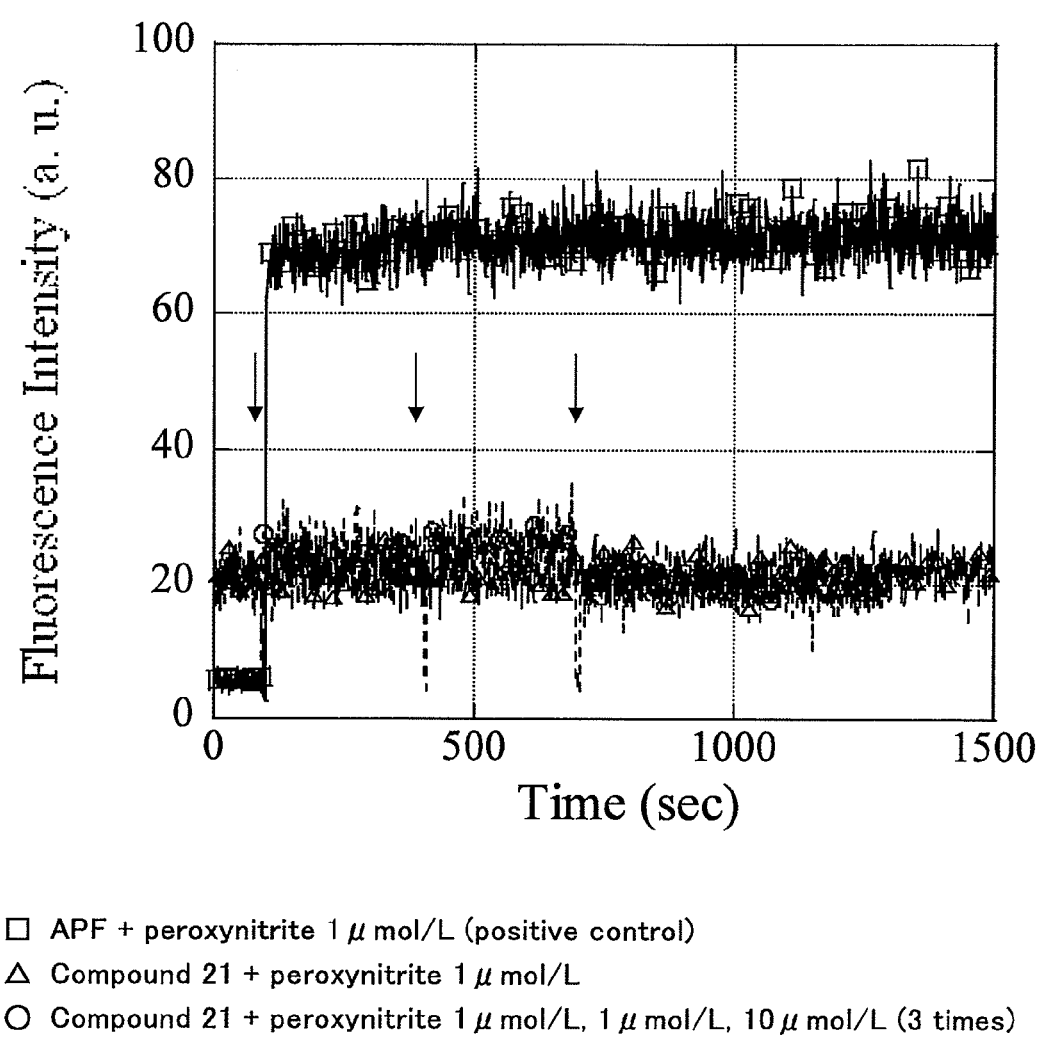
☐ APF + peroxynitrite 1 μ mol/L (positive control)
△ Compound 21 + peroxynitrite 1 μ mol/L
○ Compound 21 + peroxynitrite 1 μ mol/L, 1 μ mol/L, 10 μ mol/L (3 times)

[Fig. 5]
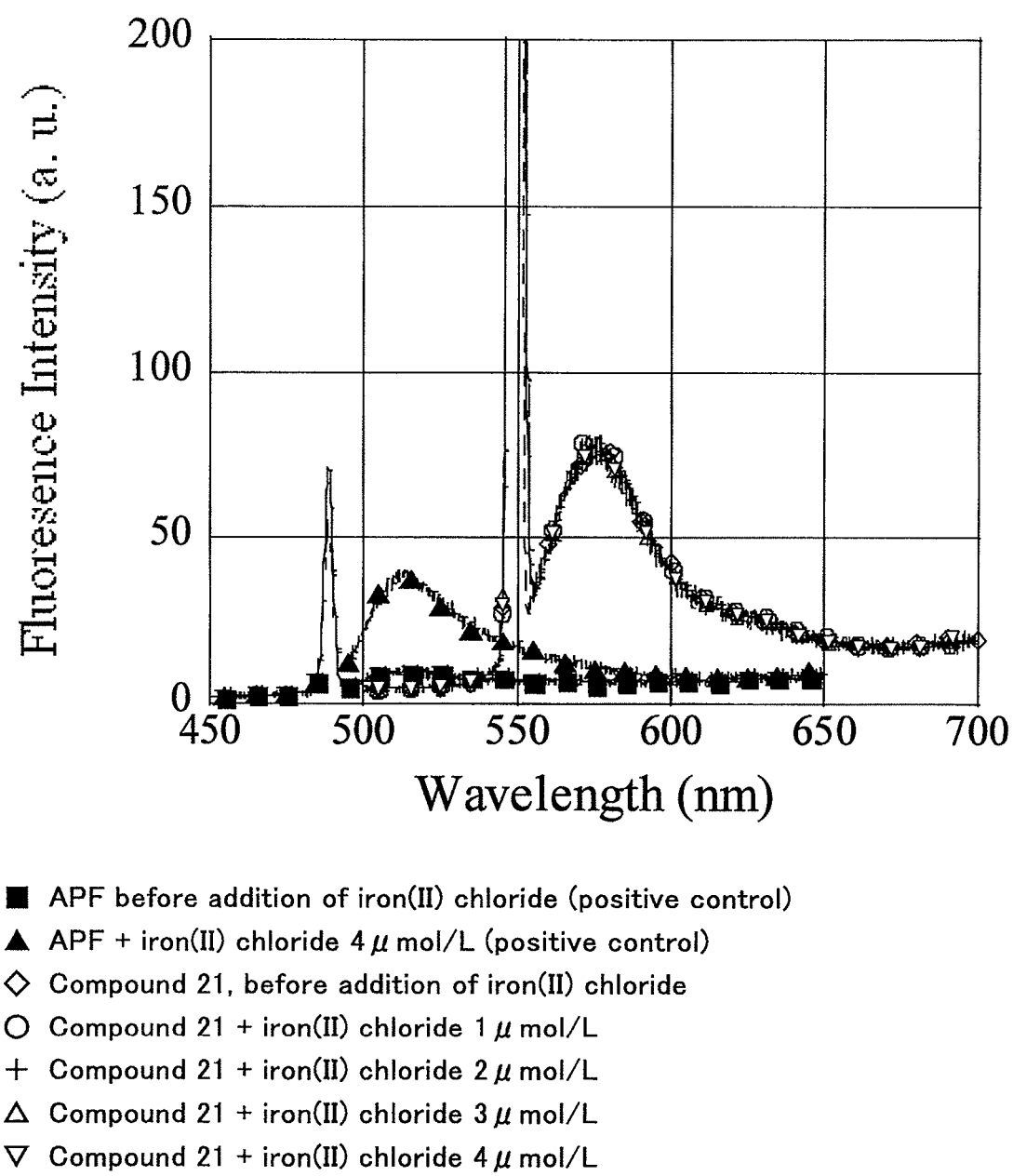
■ APF before addition of iron(II) chloride (positive control)
▲ APF + iron(II) chloride 4 μ mol/L (positive control)
◇ Compound 21, before addition of iron(II) chloride
○ Compound 21 + iron(II) chloride 1 μ mol/L
+ Compound 21 + iron(II) chloride 2 μ mol/L
△ Compound 21 + iron(II) chloride 3 μ mol/L
▽ Compound 21 + iron(II) chloride 4 μ mol/L

[Fig. 6]
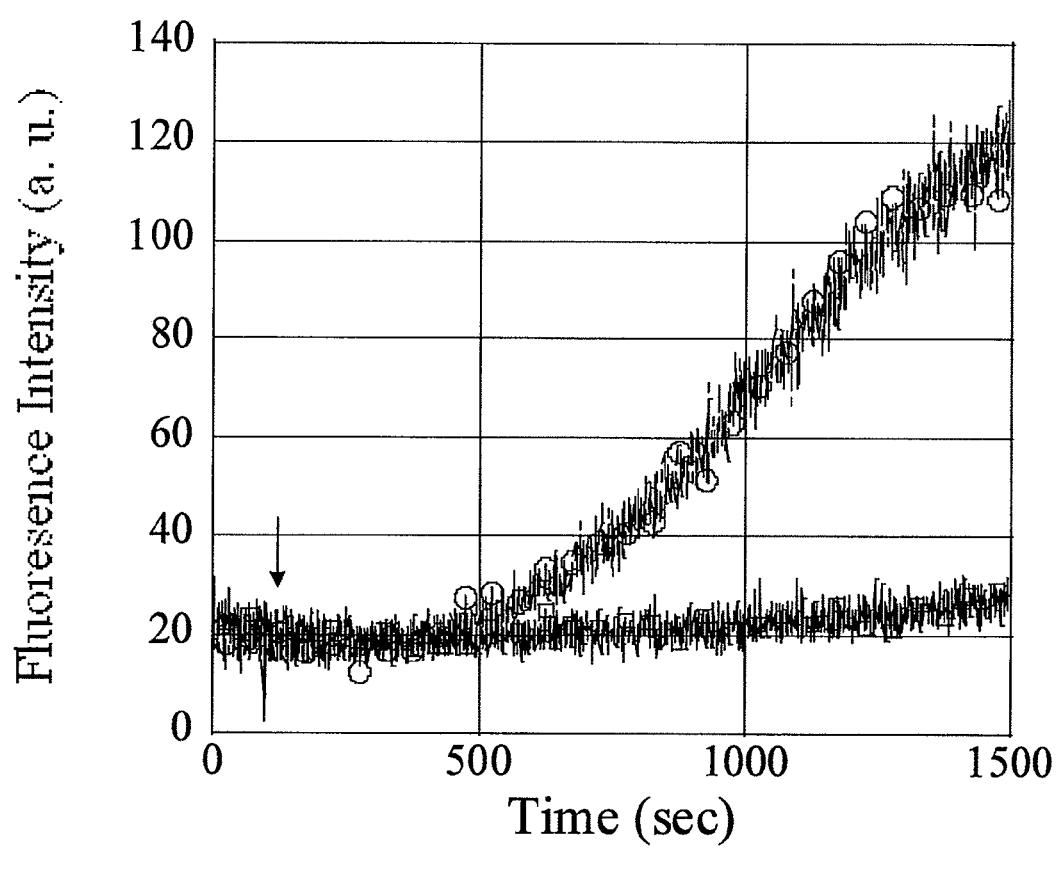
☐ DMF (negative control)
◯ PMA 2 ng/mL

FLUORESCENT PROBE AND METHOD OF MEASURING HYPOCHLORITE ION

TECHNICAL FIELD

The present invention relates to a novel compound usable as a fluorescent probe useful for selective measurement of hypochlorite ion and the like, and a fluorescent probe which comprises said compound.

BACKGROUND ART

Hypochlorite ion is one of the reactive oxygen species of which actions in living bodies have been attracting attention in recent years. It is thought that the bactericidal action of neutrophils is mainly based on hypochlorite ions, and it has been demonstrated in vitro that hypochlorite ion is generated from hydrogen peroxide and chloride ion by myeloperoxidase in the azurophil granules (Klebanoff, S. J., and Clark, R. A. (1978), The Neutrophils: Function and Clinical Disorders, North-Holland Publishing Company, Amsterdam, Netherlands). Moreover, it is considered that hypochlorite ion plays an important role in injury of vascular endothelial surface in microcirculation dysfunction induced by the platelet activating factor (Suematsu, M., Kurose, I., Asako, H., Miura, S., and Tsuchiya, M. (1989) J. Biochem., 106, 355-360). However, since any perfect method of selectively measuring hypochlorite ions, especially in vivo measurement method, has not been established, it has been difficult to conclude that hypochlorite ion is directly involved in the aforementioned mechanism in living bodies.

It is thought that obstruction by reactive oxygen species over various physiologically active molecules and the like is involved in various diseases. Among these, reactive oxygen species having high oxidation ability such as hypochlorite ion, peroxynitrite, and hydroxyl radical give serious obstructions to living bodies, and therefore it is desired to provide a method for measuring these species in biosamples in living state with high sensitivity. Several fluorescent probes which can measure reactive oxygen species such as peroxynitrite and hydroxyl radical have hitherto been provided. For example, as a fluorescent probe for measuring reactive oxygen species, DCFH (2',7'-dichlorodihydrofluorescein) and the like are known. However, DCFH cannot identify differences between reactive oxygen species, and is not capable of selectively measuring hypochlorite ion. Although it is known that hypochlorite ion can be measured by using the compounds disclosed in International Patent Publication WO01/64664 (Setsukinai, K., et al., J. Biol. Chem., 278, pp. 3170-3175, 2003), a combination of measurements may be needed to identify hypochlorite ion, and thus it has a problem that the operation is complicated.

Non-patent document 1: J. Biol. Chem., 278, pp. 3170-3175, 2003

DISCLOSURE OF THE INVENTION

Object to be Achieved by the Invention

An object of the present invention in to provide a compound useful for selective measurement of hypochlorite ion, and the like.

Means for Achieving the Object

The inventors of the present invention conducted various researches in order to achieve the aforementioned object, and as a result, found that the compounds represented by the following general formula (I) were useful for measurement of hypochlorite ion and the like, and in particular, found that the rhodamine-like compounds did not react with hydrogen peroxide which is a weakly reactive oxygen species, and did not induce increase of fluorescence with hydroxyl radical or peroxynitrite which are reactive oxygen species having high activity, and thereby with these compounds extremely highly selective measurement of hypochlorite ion was achieved. The present invention was accomplished on the basis of the aforementioned finding.

The present invention thus provides a compound represented by the following general formula (I):

[Formula 1]

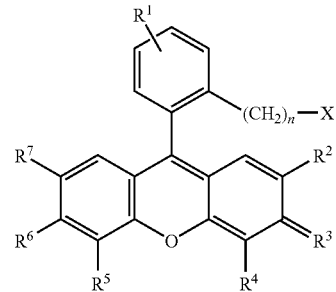

(I)

[wherein $R^1$ represents hydrogen atom or one to four monovalent substituents substituting on the benzene ring, and when it represents two or more substituents, they may be the same or different; $R^2$, $R^4$, $R^5$, and $R^7$ independently represent hydrogen atom, or a monovalent substituent; $R^3$ represents =O or =$N^+(R^8)(R^9)$.$M^-$ (wherein $R^8$ and $R^9$ independently represent an alkyl group which may be substituted, and $M^-$ represents a counter ion); $R^6$ represents —OH or —$N(R^{10})(R^{11})$ (wherein $R^{10}$ and $R^{11}$ independently represent an alkyl group which may be substituted), provided that when $R^3$ is =O, $R^6$ is —OH, and when $R^3$ is =$N^+(R^8)(R^9)$.$M^-$, $R^6$ is —$N(R^{10})(R^{11})$; n represents an integer of 1 to 3; and X represents —SH or —OH], or the following general formula (II):

[Formula 2]

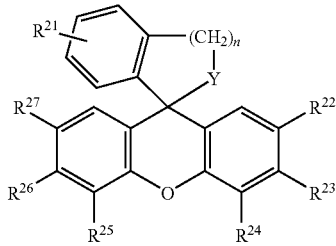

(II)

[wherein $R^{21}$ represents hydrogen atom or one to four monovalent substituents substituting on the benzene ring, and when it represents two or more substituents, they may be the same or different; $R^{22}$, $R^{24}$, $R^{25}$, and $R^{27}$ independently represent hydrogen atom, or a monovalent substituent; $R^{23}$ represents —OH or —$N(R^{28})(R^{29})$ (wherein $R^{28}$ and $R^{29}$ independently represent an alkyl group which may be substituted); $R^{26}$ represents —OH or —$N(R^{30})(R^{31})$ (wherein $R^{30}$ and $R^{31}$ independently represent an alkyl group which may be substituted), provided that when $R^{23}$ is —OH, $R^{26}$ represents —OH, and when $R^{23}$ is —N($R^{28}$)($R^{29}$), $R^{26}$ is —N($R^{30}$)($R^{31}$); n represents an integer of 1 to 3; and Y represents —S— or —O—], or a salt thereof.

According to preferred embodiments, there are provided the aforementioned compound represented by the aforementioned general formula (I) or a salt thereof, wherein $R^3$ is =$N^+$($R^8$)($R^9$).$M^-$, n is 1, and X is —SH; the aforementioned compound represented by the aforementioned general formula (I) or a salt thereof, wherein $R^3$ is =$N^+$($CH_3$)$_2$.$M^-$, n is 1, and X is —SH; the aforementioned compound represented by the aforementioned general formula (I) or a salt thereof, wherein $R^3$ is =$N^+$($R^8$)($R^9$).$M^-$, n is 1, and X is —OH; the aforementioned compound represented by the aforementioned general formula (I) or a salt thereof, wherein $R^3$ is =$N^+$($CH_3$)$_2$.$M^-$, n is 1, and X is —OH; the aforementioned compound represented by the aforementioned general formula (I) or a salt thereof, wherein $R^3$ is =O, n is 1, and X is —OH; the aforementioned compound represented by the aforementioned general formula (I) or a salt thereof, wherein $R^3$ is =O, n is 2, and X is —OH; the aforementioned compound represented by the aforementioned general formula (II) or a salt thereof, wherein $R^{23}$ is —N($R^{28}$)($R^{29}$), n is 1, and Y is —S—; the aforementioned compound represented by the aforementioned general formula (II) or a salt thereof, wherein $R^{23}$ is —N($CH_3$)$_2$, n is 1, and Y is —S—; the aforementioned compound represented by the aforementioned general formula (II) or a salt thereof, wherein $R^{23}$ is —N($R^{28}$)($R^{29}$), n is 1, and Y is —O—; the aforementioned compound represented by the aforementioned general formula (II) or a salt thereof, wherein $R^{23}$ is —N($CH_3$)$_2$, n is 1, and Y is —O—; the aforementioned compound represented by the aforementioned general formula (II) or a salt thereof, wherein $R^{23}$ is —OH, n is 1, and Y is —O—; and the aforementioned compound represented by the aforementioned general formula (II) or a salt thereof, wherein $R^{23}$ is =O, n is 2, and Y is —O—.

From another aspect, the present invention provides a fluorescent probe comprising a compound represented by the aforementioned general formula (I) or general formula (II), or a salt thereof. This fluorescent probe can be used as a probe for measurement of hypochlorite ion, a pH probe, or the like. In particular, the aforementioned fluorescent probe comprising a compound represented by the aforementioned general formula (II) or a salt thereof, wherein $R^{23}$ is —N($R^{28}$)($R^{29}$), and Y is —S— is useful as a selective fluorescent probe for hypochlorite ion. Further, the aforementioned fluorescent probe comprising the aforementioned compound represented by the aforementioned general formula (I) or a salt thereof, wherein $R^3$ is =O, and X is —OH, the aforementioned fluorescent probe comprising the aforementioned compound represented by the aforementioned general formula (I) or a salt thereof, wherein $R^3$ is =$N^+$($R^8$)($R^9$).$M^-$, and X is —OH, the aforementioned fluorescent probe comprising the aforementioned compound represented by the aforementioned general formula (II) or a salt thereof, wherein $R^{23}$ is —OH, and Y is —O—, and the aforementioned fluorescent probe comprising the aforementioned compound represented by the aforementioned general formula (II) or a salt thereof, wherein $R^{23}$ is —N($R^{28}$)($R^{29}$), and X is Y is —O— are useful as pH probes. The present invention also provides use of a compound represented by the aforementioned general formula (I) or general formula (II), or a salt thereof for manufacture of the aforementioned fluorescent probe. In these probes, n is preferably 1 or 2.

From a further aspect, there is provided a method for measuring hypochlorite ion, which comprises the steps of contacting the aforementioned compound represented by the aforementioned general formula (II) or a salt thereof having a dihydrothiophene ring structure, wherein $R^{23}$ is —N($R^{28}$)($R^{29}$), and Y is —S— with a sample, and measuring fluorescence generated from a quinoid type compound or a salt thereof generated by oxidation of the dihydrothiophene ring moiety by a reaction with hypochlorite ion in the sample.

Effect of the Invention

The compound represented by the aforementioned general formula (I) or general formula (II) or a salt thereof provided by the present invention can be used as a fluorescent probe for measurement of hypochlorite ion, a fluorescent probe as a pH probe, and the like. In particular, the aforementioned fluorescent probe comprising the aforementioned compound represented by the aforementioned general formula (II) or a salt thereof, wherein $R^{23}$ is —N($CH_3$)$_2$, n is 1, and Y is —S— has high reactivity to hypochlorite ion, but does not substantially react with other reactive oxygen species such as hydrogen peroxide, hydroxyl radical, and peroxynitrite, and thus it is extremely useful as a selective fluorescent probe for hypochlorite ion for measurement in a biosample, and the like.

BRIEF DESCRIPTION OF THE DRAWINGS

FIG. 1 depicts graphs showing pH characteristics of Compounds 8, 9, 11, 13, 19, and 21. (A) shows change of fluorescence intensity depending on pH. (B) shows change of molar extinction coefficient depending on pH.

FIG. 2 is a graph showing results of measurement of fluorescence spectrum of Compound 21 observed when hydrogen peroxide and sodium hypochlorite were added to the compound.

FIG. 3 is a graph showing results of measurement of fluorescence intensity change of Compound 21 with passage of time observed when hydrogen peroxide and sodium hypochlorite were added to the compound. The arrow in the graph indicates addition point of the reactive oxygen species.

FIG. 4 is a graph showing results of measurement of fluorescence intensity change of Compound 21 and APF observed when peroxynitrite was added to the compounds. The arrows in the graph indicate addition points of peroxynitrite.

FIG. 5 shows results of measurement of fluorescence spectra of Compound 21 and APF observed when they were reacted with hydroxyl radical.

FIG. 6 shows results of measurement of hypochlorite ion in porcine neutrophiles. The arrow (100 seconds) in the graph indicates addition point of PMA or DMF (negative control).

BEST MODE FOR CARRYING OUT THE INVENTION

In this specification, type of the "monovalent substituent" is not particularly limited, and an arbitrary substituent may be used. Examples include, for example, a halogen atom (in this specification, the "halogen atom" may be any of, for example, fluorine atom, chlorine atom, bromine atom and iodine atom), a lower alkyl group of around $C_{1-6}$ (in this specification, the "alkyl group" may be a linear, branched, or cyclic alkyl group, or an alkyl group consisting of a combination thereof, and the same shall apply to an alkyl moiety of other substituents having the alkyl moiety), a halogenated lower alkyl group of around $C_{1-6}$, a lower hydroxyalkyl group of around $C_{1-6}$, a lower alkoxy group of around $C_{1-6}$, hydroxy group, thiol group, carboxy group, alkoxycarbonyl group, an amino group (the amino group may have 1 or 2 substituents such as an alkyl group), and the like, but are not limited to these examples.

$R^1$ and $R^{21}$ represent hydrogen atom or one to four monovalent substituents substituting on the benzene ring, and when they represent two or more substituents, they may be the same or different. The substituting position of the substituent represented by $R^1$ or $R^{21}$ is not particularly limited, and it can substitute at an arbitrary substitutable position on the benzene ring.

In $R^3$, $M^-$ represents a counter ion, and means counter ions in a number for neutralizing the charge of the molecule. Although type of the counter ion is not particularly limited, examples include, chloride ion, sulfate ion, nitrate ion, organic acid anions such as methanesulfonate anion, p-toluenesulfonate anion, oxalate anion, citrate anion, tartrate anion, and the like. A carboxy anion of amino acid such as glycine may also be used.

Symbol n is preferably 1 or 2, particularly preferably 1.

As the compounds represented by the general formula (I), preferred compounds are those wherein $R^1$ is hydrogen atom, and each of $R^2$, $R^4$, $R^5$, and $R^7$ is hydrogen atom, a halogen atom, or a lower alkyl group of around $C_{1-6}$.

In particular, by substitution of $R^2$, $R^4$, $R^5$, and $R^7$ with a halogen atom, pH characteristics of the compounds of the present invention may sometimes be changed to have desired characteristics.

When X is —SH, it is preferred that $R^3$ is =$N^+(R^8)(R^9)$.$M^-$.

When X is —OH, it is preferred that $R^3$ is =$N^+(R^8)(R^9)$.$M^-$, or $R^3$ is =O.

More preferred compounds are those wherein $R^3$ is =$N^+(R^8)(R^9)$.$M^-$, n is 1, and X is —SH, and particularly preferred compounds are those wherein $R^3$ is =$N^+(CH_3)_2$.$M^-$, n is 1, and X is —SH. Other preferred compounds are those wherein $R^3$ is =$N^+(R^8)(R^9)$.$M^-$, n is 1, and X is —OH, those wherein $R^3$ is =O, n is 1, and X is —OH, and those wherein $R^3$ is =O, n is 2, and X is —OH, provided that when $R^3$ is =$N^+(R^8)(R^9)$.$M^-$, $R^6$ is —$N(R^{10})(R^{11})$, more preferably $R^6$ is —$N(CH_3)_2$, and when $R^3$ is =O, $R^6$ is —OH.

As the compounds represented by the general formula (II), preferred compounds are those wherein $R^{21}$ is hydrogen atom, and each of $R^{22}$, $R^{24}$, $R^{25}$, and $R^{27}$ is hydrogen atom, a halogen atom, or a lower alkyl group of around $C_{1-6}$. In particular, by substitution of $R^{22}$, $R^{24}$, $R^{25}$, and $R^{27}$ with a halogen atom, pH characteristics of the compounds of the present invention may sometimes be changed to have desired characteristics.

When Y is —S—, it is preferred that $R^{23}$ is —$N(R^{28})(R^{29})$.

When Y is —O—, it is preferred that $R^{23}$ is —$N(R^{28})(R^{29})$, or —OH.

More preferred compounds are those wherein $R^{23}$ is —$N(R^{28})(R^{29})$, n is 1, and Y is —S—, and particularly preferred compounds are those wherein $R^{23}$ is —$N(CH_3)_2$, n is 1, and Y is —S—. Other preferred compounds are those wherein $R^{23}$ is —$N(R^{28})(R^{29})$, n is 1, and Y is —O—, those wherein $R^{23}$ is —OH, n is 1, and Y is —O—, and those wherein $R^{23}$ is —OH, n is 2, and Y is —O—, provided that when $R^{23}$ is —$N(R^{28})(R^{29})$, $R^{26}$ is —$N(R^{30})(R^{31})$, more preferably $R^{26}$ is —$N(CH_3)_2$, and when $R^{23}$ is —OH, $R^{26}$ is —OH.

The compounds of the present invention may form a salt depending on type of substituent. Type of the salt is not particularly limited, and the salt may be an acid addition salt, or a base addition salt. As a salt of the compounds of the present invention, a physiologically acceptable salt is preferred. Although type of the salt is not particularly limited, examples include, for example, acid addition salts including mineral acid salts such as hydrochlorides, sulfates, and nitrates, and organic acid salts such as tartrates, p-toluenesulfonates, malates, oxalates and acetates; metal salts such as sodium salts, potassium salts, magnesium salts, and calcium salts; ammonium salts; organic amine salts such as monomethylamine salts and triethylamine salts; and the like. But type of the salt is not limited to these examples. The compounds of the present invention or salts thereof may form a hydrate or a solvate, and arbitrary hydrates and solvates are fall within the scope of the present invention.

The compounds of the present invention may have one or more asymmetric carbons depending on type of substituent, and the like. Stereoisomers of pure forms such as enantiomers and diastereoisomers based on one or more asymmetric carbons, arbitrary mixtures of stereoisomers such as racemic mixture and mixtures of diastereoisomers, and the like also fall within the scope of the present invention. It will be readily understood by those skilled in the art that the compounds represented by the general formula (I) or the general formula (II) are tautomers. Arbitrary mixtures of these tautomers also fall within the scope of the present invention.

Although it is not intended to be bound by any specific theory, for example, a compound represented by the general formula (I) wherein $R^3$ is =$N^+(CH_3)_2$.$M^-$, n is 1, and X is —SH, and a compound represented by the general formula (II) wherein $R^{23}$ is —$N(CH_3)_2$, n is 1, and Y is —S— are in an equilibrium in an aqueous solution environment, but at a physiological pH, most of the molecules thereof exist as ring-closed compounds represented by the general formula (II). The ring-closed compounds represented by the general formula (II) are non-fluorescent, whereas the ring-opened compounds represented by the general formula (I) are fluorescent.

By using the aforementioned characteristics, a compound represented by the aforementioned general formula (II) wherein $R^{23}$ is —$N(R^{28})(R^{29})$ (preferably $R^{23}$ is —$N(CH_3)_2$), and Y is —S— can be used as a selective fluorescent probe for hypochlorite ion. This compound has the ring-closed structure at a physiological pH and thus is substantially non-fluorescent, and it specifically reacts with hypochlorite ion, so that the dihydrothiophene ring is opened to give a strongly fluorescent compound. Since the reaction of this compound represented by the aforementioned general formula (II) wherein $R^{23}$ is —$N(R^{28})(R^{29})$ (preferably $R^{23}$ is —$N(CH_3)_2$), and Y is —S— and hypochlorite ion is advanced by oxidation of the dihydrothiophene ring by hypochlorite ion, the compound which ring is opened after the reaction with hypochlorite ion is different from the compound of the general formula (I) wherein X is —SH, and the ring thereof is not closed at a physiological pH. Further, this reaction specifically advances in the presence of hypochlorite ion, and dose not advance in the presence of other reactive oxygen species (for example, reactive oxygen species having high activity such as hydroxyl radical and peroxynitrite, or weakly reactive oxygen species such as hydrogen peroxide). Therefore, a compound represented by the aforementioned general formula (II) or a salt thereof can be used as a selective fluorescent probe for measurement of hypochlorite ion.

The term "measurement" used in this present specification should be construed in its broadest sense, including determinations, tests, and detections performed for the purpose of quantification, qualification, diagnosis or the like. The method for measurement of a measuring object using the fluorescent probe of the present invention generally comprises (a) the step of contacting a compound represented by the aforementioned formula (II) wherein $R^{23}$ is —$N(R^{28})(R^{29})$, and Y is —S— or a salt thereof with a sample; and (b)

the step of measuring fluorescence generated by a reaction with hypochlorite ion in the sample. For example, the fluorescent probe of the present invention or a salt thereof may be dissolved in an aqueous medium such as physiological saline or a buffer, or in a mixture of an aqueous medium and a water-miscible organic solvent such as ethanol, acetone, ethylene glycol, dimethyl sulfoxide, and dimethylformamide, the resultant solution may be added to a suitable buffer containing cells or tissues, and then the fluorescence spectra may be measured.

Further, although it is not intended to be bound by any specific theory, a compound represented by the general formula (I) wherein $R^3$ is =O, and X is —OH and a compound represented by the general formula (II) wherein $R^{23}$ is —OH, and Y is —O— are in an equilibrium in an aqueous solution, and the fluorescent property thereof is changed by protonation. For example, a compound represented by the general formula (I) wherein $R^3$ is =O, n is 1, and X is —OH and a compound represented by the general formula (II) wherein $R^{23}$ is —OH, n is 1, and Y is —O— are in the following equilibrium in an aqueous solution, and the fluorescent property thereof changes in a pH-dependent manner. Therefore, a compound represented by the general formula (I) wherein $R^3$ is =O, and X is —OH and a compound represented by the general formula (II) wherein $R^{23}$ is —OH, and Y is —O— can be used as a pH-dependent fluorescent probe.

[Formula 3]

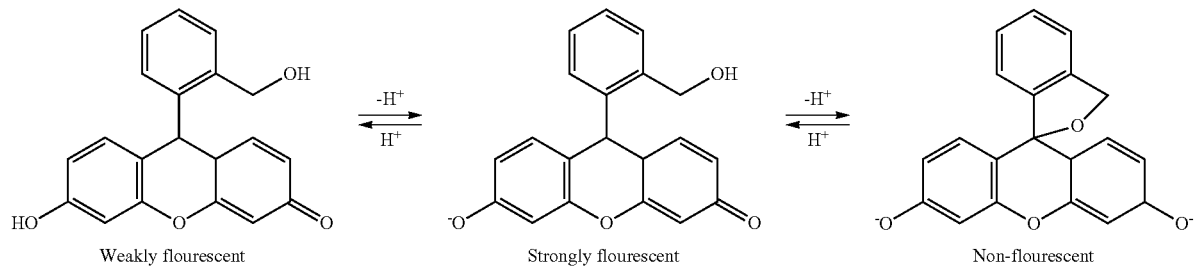

Weakly flourescent     Strongly flourescent     Non-flourescent

Fluorescence emitted from the compounds of the present invention can be measured by an ordinary method. For example, a method of measuring fluorescence spectra in vitro, a method of measuring fluorescence spectra in vivo by using a bioimaging technique, and the like can be employed. For example, when a quantitative measurement is conducted, it is desirable that a calibration curve is prepared beforehand in a conventional manner.

The fluorescent probe of the present invention may be used as a composition by mixing with additives generally used for preparation of measurement reagents, if necessary. For example, as additives for use of regents under a physiological condition, additives such as dissolving aids, pH adjusters, buffers, and isotonic agents can be used, and amounts of these additives can suitably be chosen by those skilled in the art. The compositions may be provided as those in appropriate forms, for example, powdery mixture, lyophilized product, granule, tablet, solution, and the like.

EXAMPLES

The present invention will be explained more specifically by referring to the following examples. However, the scope of the present invention is not limited to these examples.

Example 1

Synthesis of Compounds 8, 9, 11 and 13

<Scheme 1>

[Formula 4]

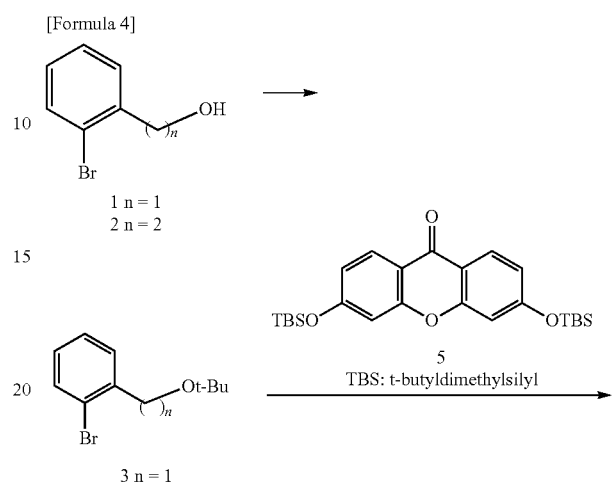

1 n = 1
2 n = 2

3 n = 1
4 n = 2

5
TBS: t-butyldimethylsilyl

-continued

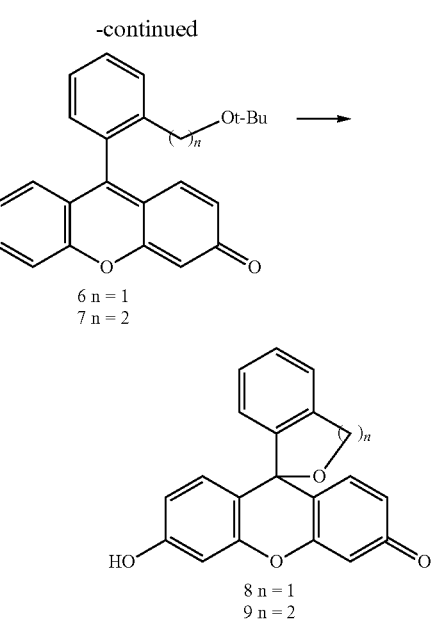

6 n = 1
7 n = 2

8 n = 1
9 n = 2

6

-continued

10

12

11

13

(A) Synthesis of Compound 3

Compound 1 (2.7 g, 15 mmol) and distilled dichloromethane (200 mL) were mixed, the mixture was bubbled with isobutene for 2 hours with stirring in an ice water bath, and added with three drops of concentrated sulfuric acid, and the mixture was stirred at room temperature for 15 hours. The reaction mixture was washed with water, and dried over anhydrous sodium sulfate. The reaction mixture was evaporated under reduced pressure, and the obtained residue was purified by silica gel column chromatography (eluent: dichloromethane) to obtain colorless acicular crystals (19.1 g, yield: 54.4%).

$^1$H NMR (300 MHz, CDCl$_3$) δ 1.31 (s, 9H), 4.50 (s, 2H), 7.11 (m, 1H), 7.31 (m, 1H), 7.50 (dd, 1H, J=8.16, 0.93 Hz), 7.55 (m, 1H).

(B) Synthesis of Compound 6

Compound 3 (0.73 g, 3 mmol) and Compound 5 (0.91 g, 2 mmol) were each dissolved in 20 mL and 40 mL of tetrahydrofuran, and each solution was added with activated molecular sieves 4A 1/16, and dried for 1 hour under an argon atmosphere. The solution of Compound 3 in tetrahydrofuran was transferred into a 2-neck flask under a sufficiently dried argon atmosphere with a syringe, and added with a solution of 1.5 mol/L t-butyllithium in n-pentane (4 mL, 6 mmol) with stirring in a dry ice/acetone bath (−80° C.), and the mixture was stirred for 30 minutes in a dry ice/acetone bath (−80° C.), and then added with the solution of Compound 5 in tetrahydrofuran. The mixture was removed from the dry ice/acetone bath, brought to room temperature, stirred for 2 hours, and added with a small volume of water. The reaction mixture was evaporated under reduced pressure, the residue was added with saturated aqueous sodium dihydrogenphosphate and ethyl acetate, and dissolved therein, the solution was extracted with ethyl acetate, and the organic layer was dried over anhydrous sodium sulfate. The solvent was evaporated under reduced pressure to obtain reddish orange oil. This oil was purified by silica gel column chromatography (eluent: ethyl acetate/methanol=20/1) to obtain orange solid (0.58 g, yield: 78%).

$^1$H NMR (300 MHz, CDCl$_3$) δ 0.81 (s, 9H), 4.13 (s, 2H), 6.82 (dd, 2H, J=2.01, 9.18 Hz), 6.86 (d, 2H, J=2.01 Hz), 7.09 (d, 2H, J=9.18 Hz), 7.20 (d, 1H, J=7.14 Hz), 7.46 (td, 1H, J=7.37, 1.41 Hz), 7.54 (m, 1H), 7.59 (d, 1H, J=7.41 Hz). $^{13}$C NMR (75 MHz, CDCl$_3$) δ 26.5, 59.7, 62.1, 72.5, 127.8, 129.3, 129.6, 130.7, 132.4, 137.4, 149.5.

HRMS (ESI-Tof) m/z Found 373.1419 (M-H)$^-$. calculated 373.1439 for C$_{24}$H$_{21}$O$_4$ (−2.04 mmu).

(C) Synthesis of Compound 8

Compound 6 (370 mg, 1 mmol) and trifluoroacetic acid (10 mL) were mixed, and the mixture was refluxed by heating at 100° C. for 16 hours, then neutralized with 2 mol/L aqueous sodium hydroxide under ice cooling, and then adjusted to pH 4 by addition of saturated aqueous sodium dihydrogenphosphate. This aqueous layer was extracted with ethyl acetate, and the organic layer was dried over anhydrous sodium sulfate, and evaporated under reduced pressure to obtain reddish orange solid. This solid was purified by silica gel column chromatography (eluent: ethyl acetate) to obtain reddish orange solid (220 mg, yield: 70%).

$^1$H NMR (300 MHz, CD$_3$OD) δ 5.13 (s, 2H), 6.39 (dd, 2H, J=7.60, 2.40 Hz), 6.48 (d, 2H, J=2.40 Hz), 6.63 (d, 2H, J=7.60 Hz), 6.72 (d, 1H, J=7.50 Hz), 7.2 (m, 1H), 7.2-7.4 (m, 2H).

HRMS (ESI-Tof) m/z Found 317.0809 (M-H)$^-$. calculated 317.0814 for C$_{20}$H$_{13}$O$_4$ (−0.51 mmu).

(D) Synthesis of Compound 4

The synthesis was performed in the same manner as that for Compound 3 mentioned above.

$^1$H NMR (300 MHz, CDCl$_3$) δ 1.16 (9H, s), 2.97 (t, 2H, J=7.52 Hz), 3.56 (t, 2H, J=7.34 Hz), 7.06 (dt, 1H, J=10.39, 3.94 Hz), 7.2-7.3 (m, 2H), 7.52 (d, 1H, J=7.70 Hz).

(E) Synthesis of Compound 7

The synthesis was performed in the same manner as that for Compound 6 mentioned above.

$^1$H NMR (300 MHz, (CD$_3$)$_2$CO) δ 0.96 (s, 9H), 2.57 (dd, 2H, J=12.8, 5.69 Hz), 3.37 (t, 2H, J=7.06 Hz), 6.57 (d, 2H, J=1.83 Hz), 6.62 (dd, 2H, J=9.17, 2.20 Hz), 6.94 (d, 2H, J=9.17 Hz), 7.28 (dd, 1H, J=7.61, 1.01 Hz), 7.46 (td, 1H, J=7.34, 1.65 Hz), 7.55 (td, 1H, J=7.43, 1.47 Hz), 7.61 (dd, 1H, J=7.61, 1.01 Hz).

HRMS (ESI-Tof) m/z Found 387.1578 (M-H)$^-$. calculated 387.1596 for C$_{25}$H$_{23}$O$_4$ (−1.83 mmu).

(F) Synthesis of Compound 9

The synthesis was performed in the same manner as that for Compound 8 mentioned above.

$^1$H NMR (300 MHz, (CD$_3$)$_2$CO) δ 2.97 (t, 2H, J=5.50 Hz), 3.81 (t, 2H, J=5.59 Hz), 6.54 (dd, 2H, J=8.53, 2.48 Hz), 6.69 (d, 2H, J=2.48 Hz), 6.70 (d, 2H, J=8.53 Hz), 6.75 (d, 1H, J=8.44 Hz), 7.10-7.13 (m, 1H), 7.26-7.28 (m, 2H), 8.68 (s, 2H).

$^{13}$C NMR (75 MHz, d$_6$DMSO) δ 48.5, 72.7, 101.9, 110.7, 117.3, 125.9, 126.6, 128.1 129.3, 130.5, 135.5, 138.7, 151.8, 157.9, 206.6.

HRMS (ESI-Tof) m/z Found 331.0948 (M-H)$^-$. calculated 331.0970 for C$_{21}$H$_{15}$O$_4$ (−2.21 mmu).

(G) Synthesis of Compound 10

Compound 6 (440 mg, 1.2 mmol) was dissolved in a mixed solution of methanol (30 mL) and 2 mol/L aqueous sodium hydroxide (30 mL), the solution was slowly added dropwise with 75 mmol/L sodium hypochlorite/2 mol/L aqueous sodium hydroxide with stirring in an ice water bath, and the mixture was added dropwise with a solution of sodium hypochlorite in an amount corresponding to 2.5 mmol with confirming red shift of the absorption peak top at 494 nm with an absorptiometer. The reaction mixture was added with ascorbic acid to scavenge excessive sodium hypochlorite, and evaporated under reduced pressure to sufficiently remove methanol, and then the residue was added with ethyl acetate and saturated aqueous sodium dihydrogenphosphate and dissolved therein. The solution was extracted with ethyl acetate, and the organic layer was dried over anhydrous sodium sulfate, and evaporated under reduced pressure to obtain reddish orange oil. This oil was purified by silica gel column chromatography (eluent: dichloromethane/methanol=20/1) to obtain reddish orange solid (62 mg, yield: 13%).

HRMS (ESI-Tof) m/z Found 409.1214 (MH)+. calculated 409.1207 for $C_{24}H_{22}ClO_4$ (+0.74 mmu).

(H) Synthesis of Compound 11

The synthesis was performed in the same manner as that for Compound 8 mentioned above.

$^1$H NMR (300 MHz, $(CD_3)_2CO$) δ 5.28 (s, 2H), 6.62 (dd, 1H, J=2.37, 8.61 Hz), 6.7-6.9 (m, 3H), 6.84 (d, 1H, J=8.61), 6.87 (d, 1H, J=7.14 Hz), 7.28 (dd, 1H, J=7.45 Hz), 7.39 (td, 1H, J=0.98, 7.45 Hz), 7.46 (d, 2H, J=7.45 Hz).

$^{13}$C NMR (75 MHz, $(CD_3)_2CO$) δ 72.8, 84.2, 102.9, 112.4, 113.1, 117.5, 119.3, 121.8, 124.3, 128.3, 128.9, 129.1, 130.8, 140.0, 146.4, 148.0, 151.8, 154.6, 159.1.

HRMS (ESI-Tof) m/z Found 351.0415 (M-H)−. calculated 351.0424 for $C_{20}H_{12}ClO_4$ (−0.51 mmu).

(I) Synthesis of Compound 12

Reddish orange solid (130 mg, yield: 24%) was obtained as another main product in the synthesis of Compound 10.

$^1$H NMR (300 MHz, $(CD_3)_2CO$) δ 0.77 (s, 9H), 4.20 (s, 2H), 6.81 (d, 2H, J=9.36 Hz), 7.04 (d, 2H, J=9.36 Hz), 7.30 (d, 1H, J=6.93 Hz), 7.6-7.5 (m, 3H).

HRMS (ESI-T of) m/z Found 441.0694 (M-H)−. calculated 441.0660 for $C_{24}H_{19}Cl_2O_4$ (+3.35 mmu).

(J) Synthesis of Compound 13

The synthesis was performed in the same manner as that for Compound 8 mentioned above.

$^1$H NMR (300 MHz, $(CD_3)_2CO$) δ 5.29 (s, 2H), 6.79 (d, 2H, J=8.97 Hz), 6.82 (d, 2H, J=8.97 Hz), 6.92 (d, 1H, J=7.50 Hz), 7.30 (td, 1H, J=1.03, 7.43 Hz) 7.41 (td, 1H, J=1.03, 7.47 Hz), 7.47 (d, 1H, J=7.50 Hz), 9.16 (s, 2H).

$^{13}$C NMR (75 MHz, $(CD_3)_2CO$) δ 73.0, 84.4, 108.5, 113.0, 118.9, 121.9, 124.3, 128.1, 129.1, 129.2, 140.0, 145.9, 147.7, 154.8.

HRMS (ESI-T of): Found 385.0019 (M-H)−. calculated 385.0034 for $C_{20}H_{11}Cl_2O_4$ (−1.56 mmu).

Example 2

Synthesis of Compound 17

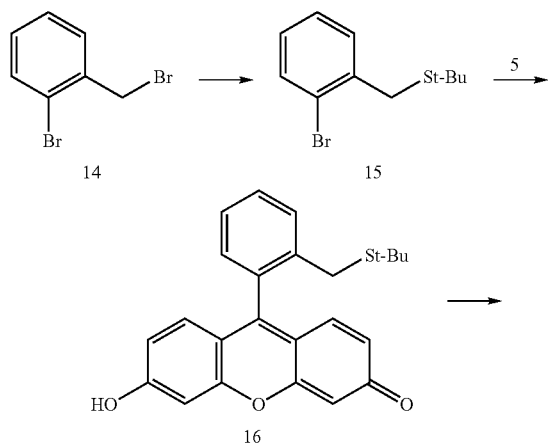

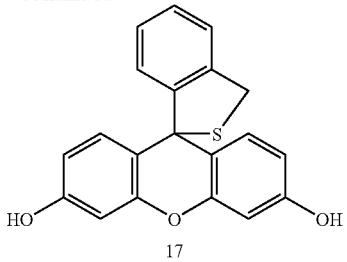

(K) Synthesis of Compound 15

Compound 14 (2.50 g, 10.0 mmol), t-butylmercaptan (1.35 g, 15.0 mmol), cesium carbonate (3.30 g, 10.0 mmol), and dimethylformamide (30 mL) were mixed, and the mixture was stirred at room temperature for 15 hours. The reaction mixture was diluted in n-hexane, washed with 0.1 mol/L sodium phosphate buffer (pH 7.4), dried over anhydrous sodium sulfate, and evaporated under reduced pressure, and the obtained residue was purified by silica gel column chromatography (eluent: n-hexane) to obtain colorless liquid (1.96 g, yield: 75.7%).

$^1$H NMR (300 MHz, $CDCl_3$) δ 1.39 (s, 9H), 3.89 (s, 2H), 7.08 (td, 1H, J=7.66, 1.71 Hz), 7.25 (td, 1H, J=7.47, 1.22 Hz), 7.44 (dd, 1H, J=7.61, 1.74 Hz), 7.53 (dd, 1H, J=8.07, 1.28 Hz).

$^{13}$C NMR (75 MHz, $CDCl_3$) δ 30.8, 33.5, 43.2, 124.4, 127.5, 128.4, 131.0, 132.9, 137.9.

(L) Synthesis of Compound 16

Compound 15 (0.38 g, 1.5 mmol) and Compound 5 (0.46 g, 1.0 mmol) were each dissolved in 20 mL of distilled tetrahydrofuran, and each solution was added with activated molecular sieves 4A 1/16, and dried under an argon atmosphere for 1 hour. The solution of Compound 15 in tetrahydrofuran was transferred into a 2-neck flask under a sufficiently dried argon atmosphere with a syringe, and added with a 1.5 mol/L solution of t-butyllithium in n-pentane (1.3 mL, 2 mmol) with stirring in a dry ice/acetone bath (−80° C.), the mixture was stirred for 10 minutes in a dry ice/acetone bath (−80° C.), and then added with the solution of Compound 5 in tetrahydrofuran, and the mixture was removed from the dry ice/acetone bath, stirred at room temperature for 30 minutes, and added with a small volume of hydrochloric acid. The reaction mixture was evaporated under reduced pressure, the residue was added with saturated aqueous sodium dihydrogenphosphate and ethyl acetate, and dissolved therein, the solution was extracted with ethyl acetate, and the organic layer was dried over anhydrous sodium sulfate, and evaporated under reduced pressure to obtain red solid. This solid was charged in a silica gel column, washed with ethyl acetate, and then eluted with methanol, the methanol fraction was evaporated under reduced pressure, and then the residue was added with aqueous sodium dihydrogenphosphate and ethyl acetate, and dissolved therein. The solution was extracted with ethyl acetate, and the organic layer was dried over anhydrous sodium sulfate, and evaporated under reduced pressure to obtain red solid (0.40 mg, quantitative).

$^1$H NMR (300 MHz, DMSO) δ 1.05 (s, 9H), 3.58 (s, 2H), 6.58 (d, 2H, J=1.65 Hz), 6.61 (dd, 2H, J=9.26, 2.11 Hz), 6.95 (d, 2H, J=8.99 Hz), 7.33 (dd, 1H, J=7.34, 1.56 Hz), 7.51 (td, 1H, J=7.38, 1.53 Hz), 7.58 (td, 1H, J=7.47, 1.59 Hz), 7.66 (dd, 1H, J=7.61, 1.38 Hz).

HRMS (ESI-T of) m/z Found 389.1197 (M-H)−. calculated 389.1211 for $C_{24}H_{21}O_3S$ (−1.46 mmu).

(M) Synthesis of Compound 17

Compound 16 (220 mg, 0.56 mmol) and trifluoroacetic acid (10 mL) were mixed, and the mixture was refluxed by heating at 100° C. for 16 hours, and evaporated under reduced pressure to remove trifluoroacetic acid. The residue was dissolved in 2 mol/L aqueous sodium hydroxide, the aqueous phase was washed with ethyl acetate, charged in an ODS silica gel column, and eluted with ultrapure water, and the obtained fraction was adjusted to pH 7 by neutralization with hydrochloric acid. The deposited yellow solid was collected by filtration to obtain yellow solid (122 mg, yield: 65%).

$^1$H NMR (300 MHz, DMSO-$d_6$) δ 4.49 (s, 2H), 6.43 (s, 2H), 6.45 (dd, 2H, J=7.98, 1.93 Hz), 6.72 (d, 1H, J=7.52 Hz), 6.77 (m, 2H), 7.20 (td, 1H, J=7.38, 0.76 Hz), 7.29 (td, 1H, J=7.52, 1.16 Hz), 7.43 (d, 1H, J=7.52 Hz), 9.73 (s, 2H).

HRMS (ESI-T of) m/z Found 333.0577 (M-H)$^-$. calculated 333.0585 for $C_{20}H_{13}O_3S$ (−0.86 mmu).

Example 3

Synthesis of Compound 19

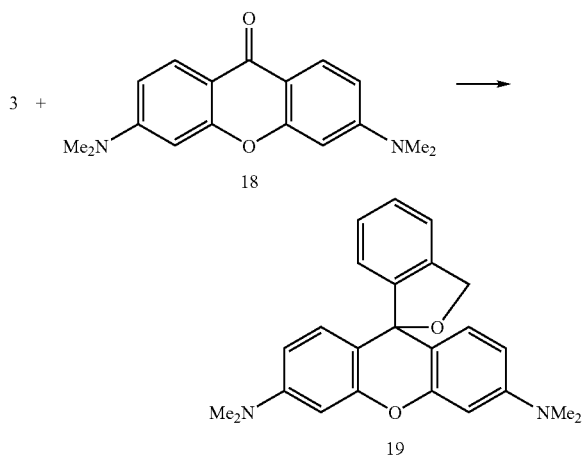

[Formula 6]

<Scheme 3>

(N) Synthesis of Compound 19

Compound 3 (0.49 g, 2 mmol) and Compound 18 (0.28 g, 1 mmol) were each dissolved in 25 mL of distilled tetrahydrofuran, and each solution was added with activated molecular sieves 4A 1/16, and dried under an argon atmosphere for 1 hour. The solution of Compound 3 in tetrahydrofuran was transferred into a 2-neck flask under a sufficiently dried argon atmosphere with a syringe, and added with a 1.5 mol/L solution of t-butyllithium in n-pentane (1.5 mL, 2.3 mmol) with stirring in a dry ice/acetone bath (−80° C.), and the mixture was stirred for 30 minutes in a dry ice/acetone bath (−80° C.), and added with the solution of Compound 18 in tetrahydrofuran. Then, the mixture was removed from the dry ice/acetone bath, returned to room temperature, stirred for 2 hours, and added with acetic acid (3 mL). The reaction mixture was evaporated under reduced pressure, the residue was added with ethyl acetate and dissolved in it, and the solution was extracted with 2 mol/L hydrochloric acid. The aqueous layer was adjusted to pH 7 by neutralization with aqueous sodium hydroxide, and extracted with dichloromethane, and the organic layer was dried over anhydrous sodium sulfate, and then evaporated under reduced pressure to obtain purple solid. This solid was purified by silica gel column chromatography (eluent: ethyl acetate), and after evaporation under reduced pressure, purple solid was obtained (4.8 mg, yield: 1.3%).

$^1$H NMR (300 MHz, $(CD_3)_2CO$) δ 2.96 (s, 12H), 5.21 (s, 2H), 6.43 (d, 2H, J=2.38 Hz), 6.47 (d, 2H, J=8.62, 2.57 Hz), 6.75 (d, 2H, J=8.62), 6.80 (d, 1H, 7.52 Hz), 7.25 (t, 1H, J=7.15 Hz), 7.36 (td, 1H, J=7.34, 0.98 Hz), 7.43 (d, 1H, J=7.52 Hz).

$^{13}$C NMR (75 MHz, $(CD_3)_2CO$) δ 40.5, 72.1, 99.1, 109.4, 114.5, 121.6, 124.4, 128.5, 128.8, 130.4, 152.3, 152.6.

HRMS (ESI-Tof) m/z Found 373.1879 (MH)$^+$. calculated 373.1916 for $C_{24}H_{25}N_2O_2$ (−3.67 mmu).

Example 4

Synthesis of Compound 21

<Scheme 4>

[Formula 7]

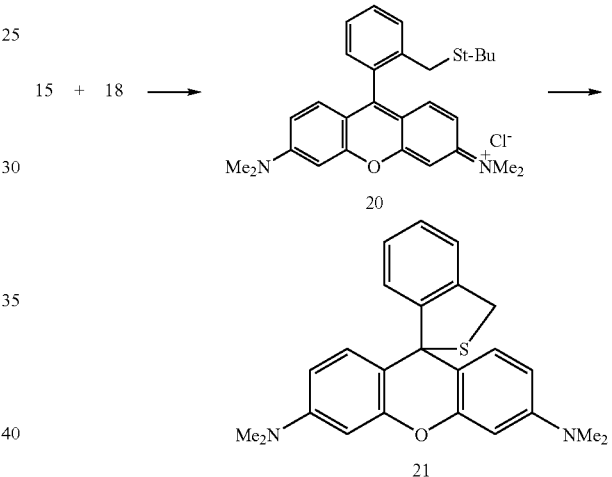

(O) Synthesis of Compound 20

Compound 15 (0.59 g, 2.4 mmol) and Compound 18 (0.28 g, 0.60 mmol) were each dissolved in 10 mL of distilled tetrahydrofuran, and each solution was added with activated molecular sieves 4A 1/16, and dried under an argon atmosphere for 1 hour. The solution of Compound 15 in tetrahydrofuran was transferred into a 2-neck flask with a syringe under a sufficiently dried argon atmosphere, and added with a 1.5 mol/L solution of t-butyllithium in n-pentane (2 mL, 3 mmol) with stirring in a dry ice/acetone bath (−80° C.), and the mixture was stirred for 10 minutes in the dry ice/acetone bath (−80° C.). Then, the mixture was added with the solution of Compound 18 in tetrahydrofuran, and the mixture was removed from the dry ice/acetone bath, returned to room temperature, stirred for 30 minutes, and added with a small volume of hydrochloric acid. The reaction mixture was evaporated under reduced pressure, the residue was added with saturated aqueous sodium dihydrogenphosphate and dichloromethane, and dissolved therein, the solution was extracted with dichloromethane, and the organic layer was dried over anhydrous sodium sulfate, and evaporated under reduced pressure to obtain reddish purple solid. This solid was dissolved in chloroform and purified by silica gel column chromatography (eluent: chloroform→ethyl acetate→dichloromethane/methanol=20/1), and after evaporation under reduced pressure, reddish purple solid was obtained (48 mg, yield: 17%).

$^1$H NMR (300 MHz, CDCl$_3$) δ 0.94 (s, 9H), 3.32 (s, 12H), 3.35 (s, 2H), 6.81 (d, 2H, J=2.4 Hz), 6.91 (dd, 2H, J=9.4, 2.5 Hz), 7.10 (dd, 1H, J=7.8, 1.0 Hz), 7.14 (d, 2H, J=9.5 Hz), 7.39 (td, 1H, J=7.4, 1.3 Hz), 7.47 (dd, 1H, J=7.7, 1.3 Hz), 7.53 (td, 1H, J=7.5, 1.2 Hz).

$^{13}$C NMR (75 MHz, CDCl$_3$) δ 30.1, 30.8, 41.0, 43.0, 96.5, 113.7, 114.2, 127.3, 129.3, 130.3, 130.7, 131.4, 131.7, 136.4, 157.1, 157.3, 157.4.

HRMS (ESI-Tof) m/z Found 445.2291 (M-Cl)$^+$. calculated 445.2314 for C$_{28}$H$_{33}$N$_2$OS (−2.27 mmu).

(P) Synthesis of Compound 21

Compound 20 (48 mg, 0.1 mmol) and trifluoroacetic acid (10 mL) were mixed, and the mixture was refluxed by heating at 100° C. for 16 hours. The mixture was neutralized with 2 mol/L aqueous sodium hydroxide under ice cooling, further added with sodium chloride and saturated with it, this aqueous layer was extracted with ethyl acetate, and the organic layer was dried over anhydrous sodium sulfate, and then evaporated under reduced pressure to obtain purple solid. This solid was purified by silica gel column chromatography (eluent: ethyl acetate), and after evaporation under reduced pressure, purple solid was obtained (24 mg, yield: 62%).

$^1$H NMR (300 MHz, CDCl$_3$) δ 2.94 (s, 12H), 4.50 (s, 2H), 6.36 (d, 2H, J=2.6 Hz), 6.40 (dd, 2H, J=8.6, 2.6 Hz), 6.87 (d, 2H, J=8.6), 6.92 (d, 1H, 7.2 Hz), 7.18 (t, 1H, J=6.9 Hz), 7.2-7.3 (m, 1H), 7.35 (d, 1H, J=7.5 Hz).

HRMS (ESI-T of) m/z Found 389.1685 (MH)$^+$. calculated 389.1688 for C$_{24}$H$_{25}$N$_2$OS (−0.22 mmu).

Example 5 pH Characteristics of Compounds 8, 9, 11, 13, 19 and 21 pH Characteristics of the compounds were investigated. DMF stock solutions of the compounds were each diluted in a 0.1 mol/L sodium phosphate buffer of arbitrary pH so that the compound concentrations and the co-solvent (dimethylformamide (DMF)) concentrations (compound concentration/DMF concentration) should be as follows.
Compound 8: 0.2 μmol/L/0.1%, Compound 9: 5 μmol/L/0.5%, Compound 11: 5 μmol/L/0.5%, Compound 13: 5 μmol/L/0.5%, Compound 19: 1.25 μmol/L/1%, Compound 21: 1 μmol/L/1%.

The results of the measurement of fluorescence intensity and molar extinction coefficient of these compounds are shown in FIG. 1. pH-dependent change of fluorescent property was observed, and accordingly it was demonstrated that these compounds successfully functioned as pH probes.

Example 6

Fluorescence Characteristics of Compound 21

A 5 μmol/L solution of Compound 21 in 0.1 mol/L sodium phosphate buffer (pH 7.4, containing 0.5% DMF as co-solvent) was added with hydrogen peroxide to adjust a final concentration to 1 mmol/L or 100 mmol/L, and sodium hypochlorite to adjust a final concentration to 2.5 μmol/L, and fluorescence spectrum was measured at an excitation wavelength of 550 nm. The results are shown in FIG. 2. Even when hydrogen peroxide was added at a high concentration, the fluorescence spectrum did not change. However, when sodium hypochlorite was added, fluorescence intensity increased at 580 nm, and significant change of fluorescence spectrum was observed. Further, in a solution not added with hydrogen peroxide and hypochlorite ion, absolutely no increase of fluorescence intensity was observed.

Example 7

Reaction of Compound 21 with Hypochlorite Ion and Hydrogen Peroxide

A 5 μmol/L solution of Compound 21 in 0.1 mol/L sodium phosphate buffer (pH 7.4, containing 0.5% DMF as a co-solvent) was added with hydrogen peroxide to adjust a final concentration to 1 mmol/L or 100 mmol/L, and sodium hypochlorite to adjust a final concentration to 2.5 μmol/L, at 25° C., and change of fluorescence intensity over time was measured at an excitation wavelength of 550 nm and emission wavelength of 580 nm. The results are shown in FIG. 3. Even when hydrogen peroxide was added at a high concentration, change of the fluorescence intensity was not observed. However, when sodium hypochlorite was added, increase of fluorescence intensity was observed.

Example 8

Reaction of Compound 21 with Peroxynitrite

In a 1 μmol/L solution of Compound 21 in 0.1 mol/L sodium phosphate buffer (pH 7.4, containing 1% DMF as co-solvent), measurement of change of fluorescence intensity over time was started at an excitation wavelength of 550 nm and emission wavelength of 580 nm at 25° C. At the time points indicated with the arrows, peroxynitrite was added to adjust a final concentration to 1 μmol/L, the same amount of peroxynitrite was further added once, and 10-fold amount of peroxynitrite was additionally added once. APF (J. Biol. Chem., 278, 3170-3175 (2003)) was also used for the measurement as a positive control, which is known to react with hypochlorite ion and peroxynitrite to show increased fluorescence intensity. The measurement using APF was performed by using a 1 μmol/L APF solution in the same manner as that for Compound 21 except that the excitation wavelength and emission wavelength for the measurement were changed to 490 nm and 515 nm, respectively, and peroxynitrite was added to adjust a final concentration to 1 μmol/L only at the time point indicated with the first arrow. The results are shown in FIG. 4. Compound 21 did not give increase of fluorescence with peroxynitrite, whilst APF showed increase of fluorescence after addition of peroxynitrite.

Example 9

Reaction of Compound 21 with hydroxyl radical

A 3 μmol/L solution of Compound 21 in 0.1 mol/L sodium phosphate buffer (pH 7.4, containing 1% DMF as co-solvent) was added with hydrogen peroxide to adjust a final concentration to 1 μmol/L. The mixture was added with an iron(II) chloride solution to adjust a final concentration to 1 μmol/L, 2 μmol/L, 3 μmol/L, and 4 μmol/L with vigorous stirring at 25° C. to generate hydroxyl radicals, and fluorescence spectrum was measured at an excitation wavelength of 550 nm. Further, comparison was made by using APF as a positive control. The measurement using APF was performed by using a 3 μmol/L APF solution in the same manner as that for Compound 21 except that the excitation wavelength and emission wavelength for the measurement were changed to 490 nm and 515 nm, respectively; and by adding the iron(II) chloride solution to adjust a final concentration to 4 μmol/L. The results are shown in FIG. 5. Compound 21 did not give difference of fluorescence spectra before and after the addition of iron(II) chloride solution, whilst APF showed increase of fluorescence intensity by the reaction with hydroxyl radicals generated by the addition of iron(II) chloride solution.

The results of Examples 6 to 9 demonstrated that Compound 21 did not cause autoxidation by light, did not react with reactive oxygen species such as hydrogen peroxide, peroxynitrite, and hydroxyl radical, and therefore successfully functioned as a probe for selectively measuring hypochlorite ion.

Example 10

Measurement of Hypochlorite Ion in Porcine Neutrophiles

Compound 21 was used for measurement of hypochlorite ions generated in porcine neutrophile upon PMA (phorbol myristate acetate) stimulation. Porcine neutrophiles purified according to the method of Wakeyama, H. et al. (Biochem. J., 205 (1982), 593-601) were suspended in the Krebs-Ringer phosphate buffer (114 mmol/L sodium chloride, 4.6 mmol/L potassium chloride, 2.4 mmol/L magnesium sulfate, 1.0 mmol/L calcium chloride, 15 mmol/L sodium dihydrogenphosphate/disodium hydrogenphosphate, pH 7.4) to adjust a density to $1 \times 10^6$ cell/mL. This cell suspension was added with Compound 21 at a concentration of 1 μmol/L (at this time, the cell suspension contained 0.1% DMF as a co-solvent), and fluorescence intensity measurement was started at 37° C. (excitation wavelength: 550 nm, emission wavelength: 580 nm). After 100 seconds, a solution of PMA in DMF was added at a PMA concentration of 2 ng/mL, and fluorometry was further continued at 37° C. (at this time, the cell suspension contained 0.2% DMF as a co-solvent). In addition, after 100 seconds, only DMF was also added at a DMF concentration of 0.2% in the cell suspension, and the measurement was performed for this mixture as a control. The results are shown in FIG. 6. Addition of DMF alone did not give increase in fluorescence intensity, but only when PMA was added, fluorescence intensity was markedly increased. From the above results, it was demonstrated that Compound 21 was capable of detecting hypochlorite ions produced by neutrophiles after PMA stimulation, and successfully functioned as a fluorescent probe for measuring hypochlorite ions.

INDUSTRIAL APPLICABILITY

The compounds represented by the aforementioned general formula (I) or (II) or salts thereof provided by the present invention can be used as fluorescent probes, such as fluorescent probes for measurement of hypochlorite ion and pH probes.

What is claimed is:
1. A compound represented by the formula (I) or a salt thereof:

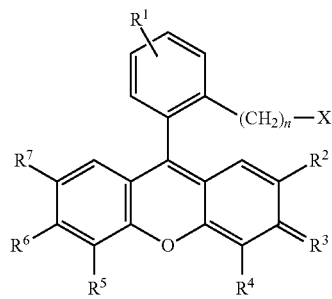

wherein $R^1$ represents hydrogen atom or one to four monovalent substituents substituting on the benzene ring, and when $R^1$ represents two or more substituents, the substituents may be the same or different; $R^2$, $R^4$, $R^5$, and $R^7$ independently represent hydrogen atom, or a monovalent substituent; $R^3$ is $=N^+(R^8)(R^9).M^-$, wherein $R^8$ and $R^9$ independently represent an alkyl group which may be substituted, and $M^-$ represents a counter ion; $R^6$ represents $-N(R^{10})(R^{11})$, wherein $R^{10}$ and $R^{11}$ independently represent an alkyl group which may be substituted; n represents an integer of 1 to 3; and X is $-SH$.

2. A compound represented by the formula (I) or a salt thereof:

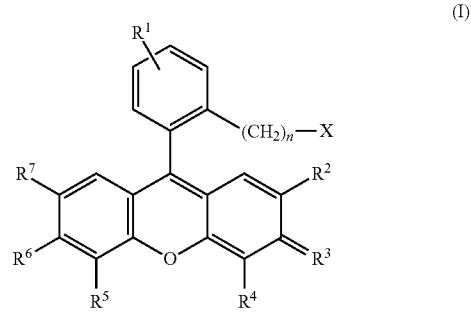

wherein $R^1$ represents hydrogen atom or one to four monovalent substituents substituting on the benzene ring, and when $R^1$ represents two or more substituents, the substituents may be the same or different; $R^2$, $R^4$, $R^5$, and $R^7$ independently represent hydrogen atom, or a monovalent substituent; $R^3$ is $=O$; $R^6$ represents $-OH$; n represents an integer of 1 to 3; and X is $-OH$.

3. A method for measuring hypochlorite ion, which comprises the following:
(a) contacting a compound represented by the following formula (II) or a salt thereof:

[Formula 2]

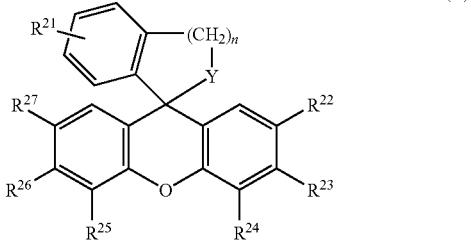

wherein $R^{21}$ represents hydrogen atom or one to four monovalent substituents substituting on the benzene ring, and when $R^{21}$ represents two or more substituents, the substituents may be the same or different; $R^{22}$, $R^{24}$, $R^{25}$, and $R^{27}$ independently represent hydrogen atom, or a monovalent substituent; $R^{23}$ is $-N(R^{28})(R^{29})$, wherein $R^{28}$ and $R^{29}$ independently represent an alkyl group which may be substituted; $R^{26}$ represents $-N(R^{30})(R^{31})$, wherein $R^{30}$ and $R^{31}$ independently represent an alkyl group which may be substituted; n represents an integer of 1 to 3; and Y is $-S-$, with a sample, and
(b) measuring fluorescence generated from a compound generated by a reaction with hypochlorite ion in the sample.

* * * * *